United States Patent
Buck et al.

(10) Patent No.: US 8,852,071 B2
(45) Date of Patent: *Oct. 7, 2014

(54) METHOD AND DEVICE FOR ACCURATE DISPENSING OF RADIOACTIVITY

(71) Applicant: Universitat Zurich, Zurich (CH)

(72) Inventors: Alfred Buck, Zurich (CH); Bruno Weber, Zurich (CH)

(73) Assignee: Bayer Medical Care Inc., Indianola, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/965,670

(22) Filed: Aug. 13, 2013

(65) Prior Publication Data

US 2013/0336881 A1    Dec. 19, 2013

Related U.S. Application Data

(62) Division of application No. 11/572,123, filed as application No. PCT/CH2005/000403 on Jul. 14, 2005, now Pat. No. 8,517,905.

(30) Foreign Application Priority Data

Jul. 16, 2004   (EP) .................................... 04405459

(51) Int. Cl.
| | |
|---|---|
| *A61N 5/00* | (2006.01) |
| *A61K 51/00* | (2006.01) |
| *A61M 5/14* | (2006.01) |
| *A61M 39/28* | (2006.01) |
| *A61M 5/00* | (2006.01) |
| *A61M 5/168* | (2006.01) |

(52) U.S. Cl.
CPC ........ *A61K 51/00* (2013.01); *A61M 2005/1403* (2013.01); *A61M 5/1407* (2013.01); *A61M 39/28* (2013.01); *A61M 5/007* (2013.01); *A61M 2205/051* (2013.01); *A61M 2210/065* (2013.01); *A61M 2205/3379* (2013.01); *A61M 5/16813* (2013.01); *A61M 5/16827* (2013.01)
USPC ............................................................. 600/1

(58) Field of Classification Search
USPC ...................................................... 600/1–8
See application file for complete search history.

(56) References Cited

U.S. PATENT DOCUMENTS

| | | |
|---|---|---|
| 4,409,966 A | 10/1983 | Lambrecht et al. |
| 4,410,108 A | 10/1983 | Minard |

(Continued)

FOREIGN PATENT DOCUMENTS

| | | |
|---|---|---|
| EP | 0486283 | 5/1992 |
| JP | 2000350783 | 12/2000 |
| JP | 2002306609 | 10/2002 |

OTHER PUBLICATIONS

International Search Report from counterpart PCT Application No. PCT/CH2005/000403.

*Primary Examiner* — John Lacyk
(74) *Attorney, Agent, or Firm* — Joseph L. Kent; David Schramm; James R. Stevenson

(57) ABSTRACT

A method of delivering a radioactive liquid, includes, performing an initialization, including; extracting at least a first amount of a radioactive liquid from a source of radioactive liquid, measuring a radioactivity level for the first amount of radioactive liquid, and performing a calibration phase. The calibration phase includes, extracting a second amount of radioactive liquid from the source of radioactive liquid wherein the second amount is calculated based on the radioactivity level of the first amount to provide a total dose of radioactive liquid having a predetermined radioactivity level, and delivering the total dose and performing at least one more calibration and delivery phases.

32 Claims, 5 Drawing Sheets

(56) References Cited

U.S. PATENT DOCUMENTS

| | | |
|---|---|---|
| 4,562,829 A | 1/1986 | Bergner et al. |
| 4,585,009 A | 4/1986 | Barker et al. |
| 6,767,319 B2 | 7/2004 | Reilly et al. |
| 7,734,331 B2 | 6/2010 | Dhawale et al. |
| 8,517,905 B2 * | 8/2013 | Buck et al. ............ 600/1 |
| 2003/0004463 A1 | 1/2003 | Reilly et al. |

* cited by examiner

METHOD AND DEVICE FOR ACCURATE DISPENSING OF RADIOACTIVITY

BACKGROUND OF THE INVENTION

The present invention relates to a device and a method for dispensing a radioactive liquid to a destination. In particular, the invention relates to the problem of accurately dispensing a well-determined dose of radioactivity, e.g., for injection to a living body.

In a number of medical applications, it is necessary to deliver a radiopharmaceutical containing a radionuclide to a patient. Due to the ionizing radiation emitted by the radionuclide, such pharmaceuticals pose a danger to both the patient and the personnel administering the radiopharmaceutical if not handled properly.

Examples for diagnostic uses of radiopharmaceuticals include positron emission tomography (PET) and single-photon emission computerized tomography (SPECT). In these methods, a patient is injected a dose of a radiopharmaceutical which can be absorbed by certain cells in the brain or in other organs. The concentration of the accumulated radiopharmaceutical in a specific body part will often depend on factors of diagnostic interest, such as cell metabolism or other physiological or biochemical processes. Thus, such processes can be imaged in a non-invasive fashion by determining the spatio-temporal distribution of radioactivity within the body part of interest. In PET, this is achieved by monitoring pairs of temporally coincident gamma rays emitted in opposite directions resulting from the annihilation of positrons, which are emitted through beta-plus decays of the (proton-rich) radionuclide. The most common radionuclides (radioisotopes) for use with PET are $^{15}O$, $^{18}F$, $^{11}C$, $^{13}N$ and $^{82}Rb$. Radiopharmaceuticals of interest for PET include, but are not limited to, substances like $[^{15}O]$—$H_2O$, $[^{18}F]$-fluorodeoxyglucose ($[^{18}F]$-FDG), $[^{18}F]$-fluoromisonidazole ($[^{18}F]$-FMISO), $[^{11}C]$-labeled amino acids, $[^{13}N]$-ammonia etc.

The most common therapeutic uses of radiopharmaceuticals are the $^{131}I$ therapies in thyroid diseases.

In these applications, it is desirable to administer an exactly determined dose of radiopharmaceutical to the body. Often the radiopharmaceutical is delivered in a vial from which it has to be dispensed into individual patient doses. In many centers this is a manual process done by the technical personnel. Since the concentration of the radiopharmaceutical in the vial can be very high, the manual dispensing is associated with considerable radiation burden to the hands. Furthermore the accuracy of the manual dispensing is limited and dependent on the experience of the person in charge.

As an example, U.S. Pat. No. 4,410,108 discloses a syringe shield equipped with a radiation detector. A liquid radiopharmaceutical is drawn from a vial into the barrel of a syringe placed within the syringe shield, while the level of radioactivity within the barrel is monitored by the radiation detector. In this way, an aliquot of the radiopharmaceutical having exactly the required dose of radioactivity can be drawn into the syringe. Subsequently, the syringe with its shield is manually removed from the vial, and the radiopharmaceutical is injected to the patient. This device is unsatisfactory in requiring manual transfer of the syringe after it has been filled with the radiopharmaceutical, as this may expose the personnel handling the syringe to ionizing radiation. Although the half-life of the radiopharmaceutical is usually rather short and the applied dosages are themselves not harmful, constant and repeated exposure over an extended period of time can be harmful.

A number of techniques have been proposed to reduce exposure by minimizing the time of exposure of personnel, by maintaining distance between personnel and the source of radiation, and by shielding personnel from the source of radiation. As an example, European patent application EP 0 486 283 discloses a system for delivering $H_2^{15}O$. A collection bottle is filled with saline, then a fluid stream comprising $H_2^{15}O$ is passed through the collection bottle while the activity in this bottle is monitored by a radiation detector. When a desired level of radiation is reached, the liquid in the bottle is transferred to a motor-driven syringe and then injected to the patient body. U.S. patent application publication No. 2003/0004463 also discloses a system for dispensing a radiopharmaceutical in a remote fashion, without the need of manual intervention. The radiopharmaceutical is drawn from a vial into a syringe surrounded by a radiation detector, and the level of radioactivity in the syringe is determined. Through specially adapted tubing and valves, the radiopharmaceutical is subsequently delivered to a patient without the need of moving the syringe to another location.

While these systems obviate the need of manual handling of a syringe, they tend to be imprecise in situations where small amounts of radioactive liquid, possibly with a very high concentration of activity, need to be handled, due to the presence of dead volumes. By the way of example, the radiopharmaceutical may come in a vial at an activity concentration of 2 GBq/ml (one billion Becquerels per milliliter). If the required activity for injection to the patient is, say, 100 MBq, a volume of just 50 microliters needs to be transferred from the vial to the patient. Such small amounts of liquid are difficult to handle with the systems of the prior art.

U.S. Pat. Nos. 4,562,829 and 4,585,009 disclose strontium-rubidium infusion systems equipped with an in-line radiation detector. A radiopharmaceutical exiting a strontium-rubidium generator flows past the radiation detector, which monitors the activity of the radiopharmaceutical in passing. From there, the radiopharmaceutical is either administered to a patient or is sent to waste. In U.S. Pat. No. 4,409,966, a flow of patient blood is shunted through a radiation detector during injection of the radiopharmaceutical, and the level of radioactivity in the blood is monitored. Also with such systems, it is difficult to administer an exactly determined dose, especially for concentrated radiopharmaceuticals with high specific activities, as the volume of the tubing already may exceed the desired volume to be injected.

SUMMARY OF THE INVENTION

It is therefore an object of the invention to provide a device which is capable of accurately dispensing a desired level of radioactivity in a liquid, and which may be operated remotely. This object is achieved by a device with features as described and claimed herein.

Thus, according to the invention, a source of a radioactive liquid and a source of a flushing liquid can be selectively connected to a fluid delivery path by way of valve means. An activity metering unit is operable to determine a level of radioactivity in a metering section of the fluid delivery path downstream from the valve means. In this way, it is possible to provide some amount, even a very small amount, of the radioactive liquid to a section of the fluid delivery path adjacent to the valve means. The flushing liquid can then be used to flush this amount of radioactive liquid to the metering section, where its activity can be determined and further steps to be taken can be decided based on this determination of activity. By use of valve means adapted for remote control (e.g. an electromagnetically or pneumatically operated valve), operation of the inventive device can be performed remotely.

It is a further object of the present invention to provide a method of operation of such a device. This object is achieved by a method with features as described and claimed herein.

Thus, according to the invention, the device is operated by transporting a first amount of radioactive liquid to the metering section, using the activity metering unit to measure a reference level of radioactivity, calculating a second amount of the radioactive liquid still to be delivered such that the first and second amounts of radioactive liquid together have some predetermined level of radioactivity, and delivering the first and second amounts of radioactive liquid to the destination. In this way, it is possible to deliver an exactly known level of radioactivity to the destination, independent of the activity concentration of the radioactive liquid. Preferably, the first amount of radioactive liquid is between 20% and 80% of the sum of the first and second amounts of radioactive liquid, more preferably between 30% and 70%, most preferably between 40% and 60%. In this way, high precision can be achieved.

In an advantageous embodiment of the inventive device, the device additionally comprises a control unit. The unit receives signals from the activity metering unit and controls operation of the valve means between at least two states. In the first state, the source of radioactive liquid is connected to the fluid delivery path for flow of the radioactive liquid into the fluid delivery path. In the second state, the source of flushing liquid is connected to the fluid delivery path for flow of flushing liquid into the fluid delivery path. If any other actively driven components are present in the device, such as additional valves or pumps, they may also be controlled by the control unit.

Advantageously, second valve means are provided downstream from the metering section for directing flow in the fluid delivery path either to the destination or to a waste reservoir. In this way it is avoided that the destination receives excessive amounts of flushing liquid during operation of the device, and in case of malfunctioning of components of the device, the radioactive liquid can be dumped to the waste reservoir.

Advantageously, a first and/or a second pump are provided for pumping the radioactive liquid or the flushing liquid, respectively, through the first valve means and into the fluid delivery path. Preferably, the first pump and/or the second pump is operable to receive a control signal and to deliver a predetermined volume of liquid based on the control signal. In this way, exactly known amounts (volumes) of the radioactive liquid and/or of the flushing liquid can be dispensed to the fluid delivery path.

The fluid delivery path may comprise a fill-in section extending from the first valve means to the metering section. Advantageously, the metering section is capable of holding a fluid volume which is at least three times, more preferably at least five times the volume of the fill-in section. This enables the metering section to hold at least two, preferably three, fractions of radioactive liquid, each with a volume up to the volume of the fill-in section, plus the flushing liquid required to flush these fractions into the metering section. Thereby, the total activity of two, preferably three, fractions of radioactive liquid may be determined in a single measurement by the activity metering unit.

Advantageously, the device is adapted for delivering a radiopharmaceutical for injection to a living body (i.e., for delivering the radiopharmaceutical to an injection needle). This encompasses, among other things, the use of compatible materials, which must be resistant to the radiopharmaceutical and the flushing liquid (usually saline solution in this case), and which must be able to withstand sterilization procedures. Such materials are well known.

As used herein, the term "pharmaceutical" refers to any substance to be injected or otherwise delivered into the body (either human or animal) in a medical procedure and includes, but is not limited to, substances used in imaging procedures and therapeutic substances. The term "radiopharmaceutical" refers to any pharmaceutical emitting ionising radiation by radioactive decay.

Further advantageous embodiments of the invention are laid down in the dependent claims. In particular, the inventive method may comprise an additional initialization procedure, in which an offset amount of radioactive liquid is transported to the metering section, an offset level of radioactivity is determined, and the predetermined level of radioactivity for the main procedure is determined from this offset level and a desired level of radioactivity to be dispensed.

BRIEF DESCRIPTION OF THE DRAWINGS

The invention will be described in more detail in connection with an exemplary embodiment illustrated in the drawings, in which.

DETAILED DESCRIPTION OF THE INVENTION

Figure 1:
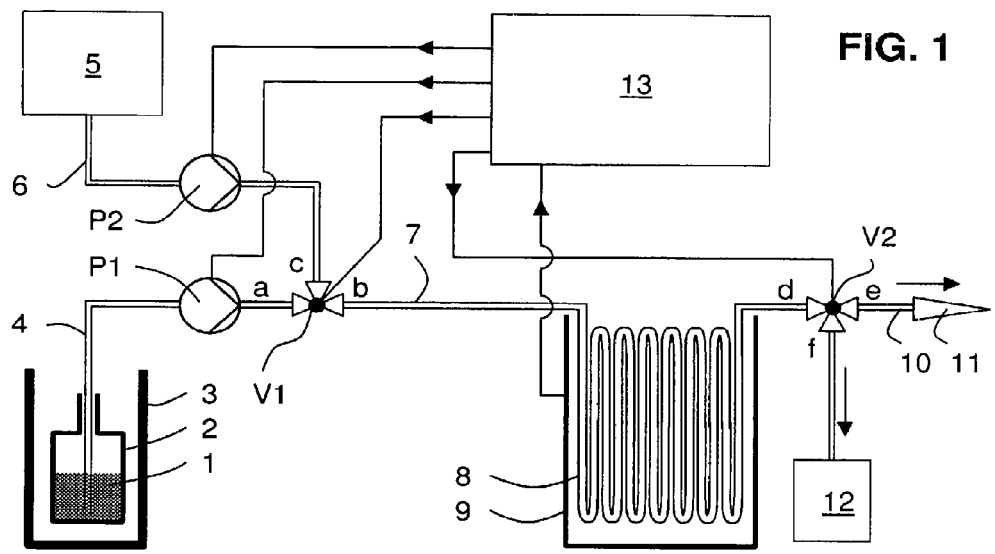
FIG. 1 shows a schematic and simplified illustration of a device according to the present invention.

FIG. 1 shows, in a highly schematic manner, a device for dispensing a radioactive liquid according to a preferred embodiment of the present invention. The device is designed for dispensing a radiopharmaceutical for injection to a patient.

The radiopharmaceutical 1 is provided in a vial 2. In order to protect the surroundings from radioactivity originating from the vial 2, the vial 2 is placed inside a shield 3. Suitable vials and shields for various kinds of radiopharmaceuticals are well known in the art and are available commercially.

A section 4 of tubing, comprising a needle at its end for puncturing a septum closing off vial 2, extends from the inside of vial 2 through a first peristaltic precision pump P1 and to a first three-way pinch valve V1. At its first port "a", the valve V1 is connected to the section 4 of tubing from the vial 2; at its second port "b", it is connected to a section of tubing 7 extending from the valve V1 to an activity metering unit 9 (in the following shortly called a "dose calibrator"). The third port "c" is connected to a section 6 of tubing leading from a saline reservoir 5 through a sec- and peristaltic precision pump P2 to the valve V1. The valve V1 is operable to connect port "a" with port "b" or to connect port "c" with port "b".

Figure 3A:
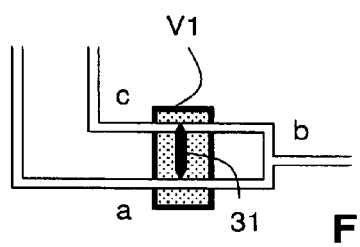
FIGS. 3A and 3B show simplified illustrations of a pinch valve.
Figure 3B:
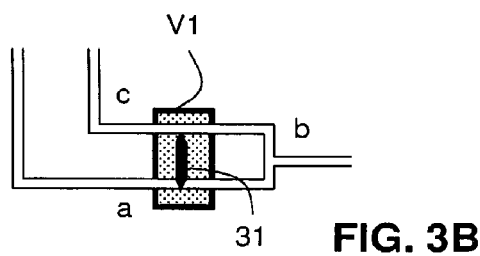

FIGS. 3A and 3B illustrate, in a highly schematic manner, the mode of operation of the pinch valve V1 as advantageously used in the present embodiment. A sliding element 31 can be moved up or down, pressing either on an upper or on a lower section of flexible tubing which is passed through the pinch valve. Thereby, either port "c" or port "a" is closed off from port "b", and the other port is connected to port "b". The sliding element 31 may, e.g., be operated electromechanically or pneumatically. A similar pinch valve is used as valve V2. Such pinch valves are advantageous because no moving parts get into contact with the liquid within the tubing. Thus the valve cannot get contaminated by radioactive liquid possibly present in the tubing.

The pumps P1 and P2 are preferably peristaltic precision pumps. In a peristaltic pump, a section of flexible tubing is passed through the pump unit. Fluid is forced along the tubing by waves of contraction produced mechanically on the flexible tubing. Peristaltic pumps offer the advantage that the liquid is always contained in the tubing, and no moving parts get into contact with the liquid to be delivered. Thus the pump itself cannot be contaminated by radioactive liquid present in the tubing. By the use of peristaltic pumps and pinch valves, the connections from the saline reservoir 5 to the metering section 7 and from the vial 2 to the metering section 7 may consist of a single piece of flexible tubing each, which can be easily replaced in regular intervals to avoid cross-contamination, without the need to replace the much more expensive pump and valve assemblies themselves.

Figure 2:
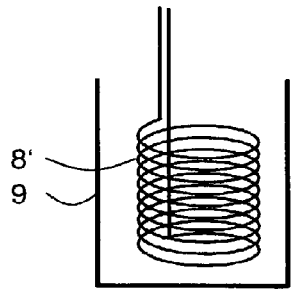
FIG. 2 shows a schematic and simplified illustration of a dose calibrator.

The section 7 of tubing may be called a "fill-in section". This fill-in section 7 is connected to a section 8 of tubing placed inside the dose calibrator 9, section 8 being called a "metering section". The metering section 8 is relatively long, providing a volume of at least five times the volume of the fill-in section, by having a meander-like shape or, preferably, a coil shape as illustrated for a metering section 8' in FIG. 2. A coil shape is preferred in practice because it minimizes pressure losses during fluid flow. The meander-like shape has been chosen in FIGS. 1 and 3-7 for illustrative purposes.

The tubing exits the dose calibrator 9 and connects to the first port "d" of a second three-way valve V2. The second port "e" of this valve is connected to a section 10 of tubing leading to an injection needle 11, only crudely symbolized by a triangle in FIG. 1. The third port "f" of valve V2 leads to a waste reservoir 12. The waste reservoir 12 is preferably shielded, as radioactivity may enter in operation.

The dose calibrator 9 is connected to a controller 13 and provides signals to the controller 13 which are indicative of the level of activity within the dose calibrator 9. The outputs of the controller 13 are connected to the pumps P1 and P2 as well as to the valves V1 and V2 for control of these.

Figure 7:
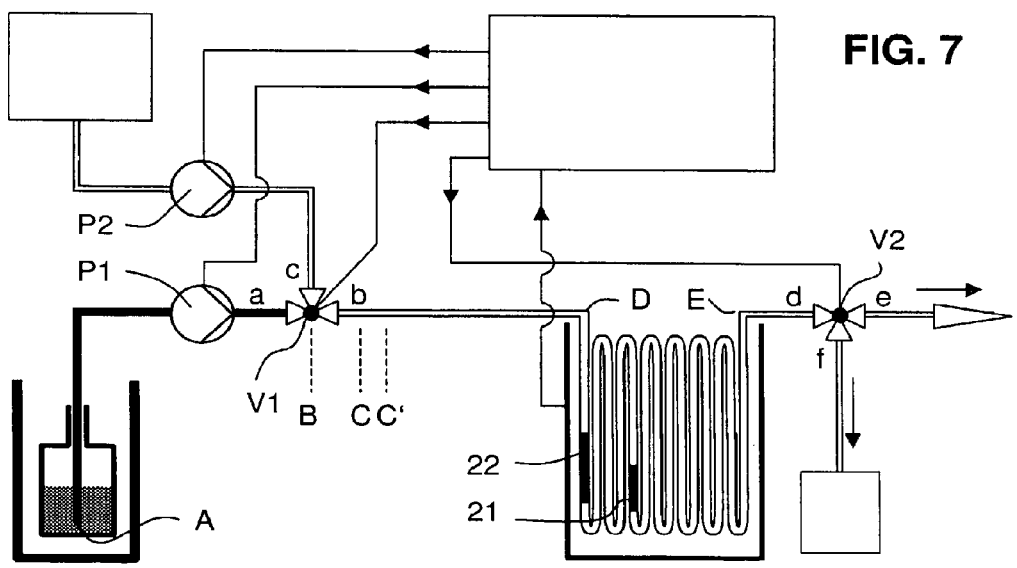
FIG. 7 illustrates a fourth state of operation of the device of FIG. 1.
Figure 8:
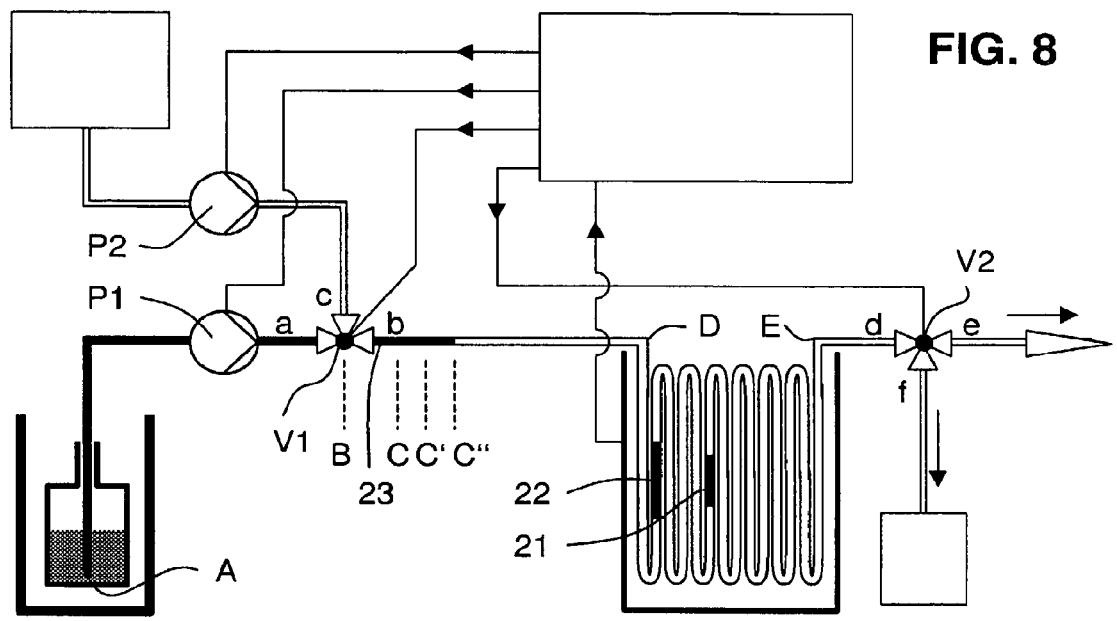
FIG. 8 illustrates a fifth state of operation of the device of FIG. 1.
Figure 9:
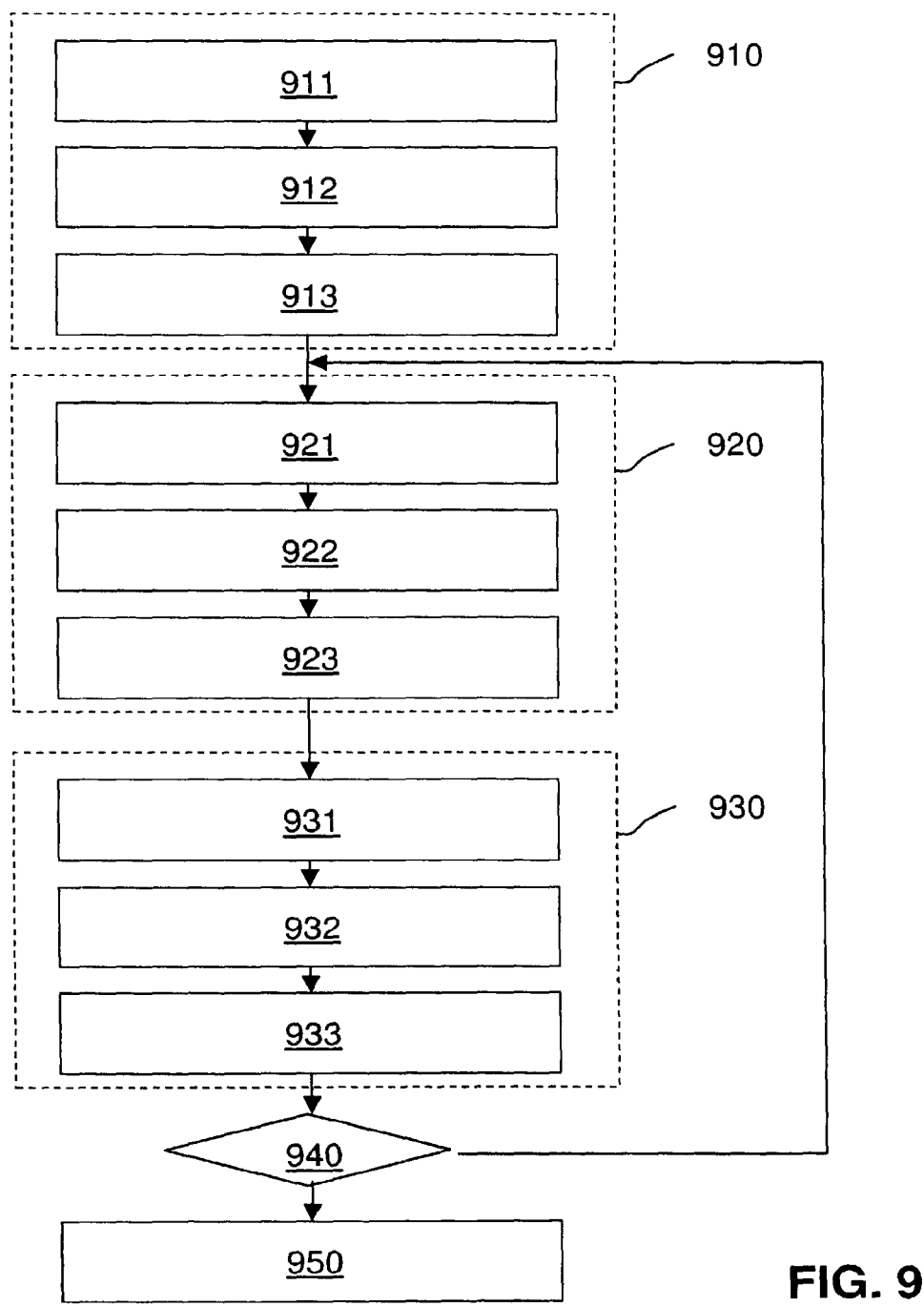
FIG. 9 shows a flow diagram of a process according to the present invention.

A method of operation of the device is illustrated in FIGS. 4 to 8 and symbolized in a flow diagram in FIG. 9. Operation can generally be divided into five phases: in an initialisation phase 910, the device is brought into a well-defined initial state. In a calibration phase 920, steps are performed for calibrating the radioactivity in vial 2. In a delivery phase 930, the radiopharmaceutical is delivered to the destination. In a step 940, it is decided whether another injection shall be performed. If yes, operation will continue again with the calibration phase 920; if not, a shutdown phase 950 will follow.

Before starting the operation, the operator will have to determine two quantities: the desired activity Ar to be injected to the patient, and the estimated concentration of activity in the vial (activity per unit of volume, e.g., expressed in MBq/ml), Cv. These data are provided to the controller 13. Operation then starts with the initialisation period 910.

Figure 4:
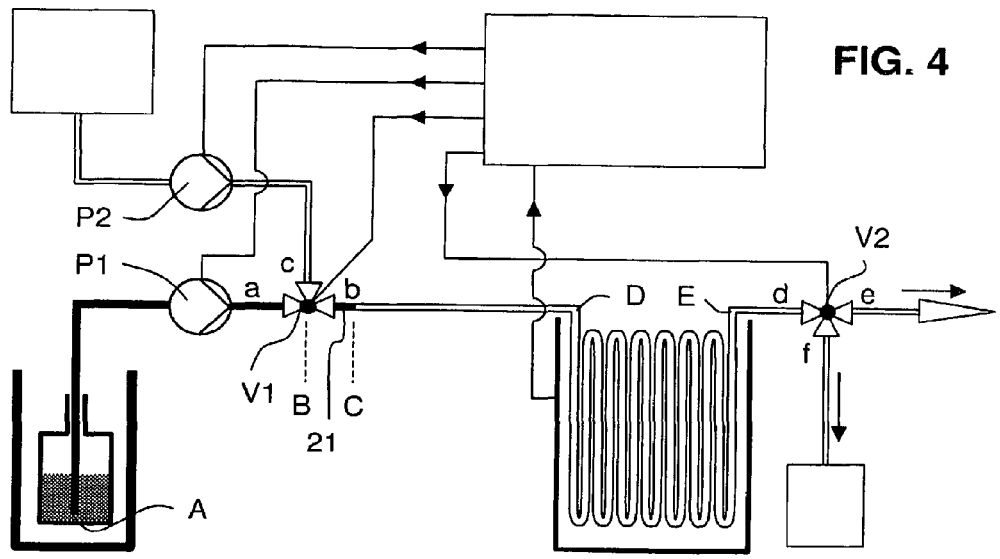
FIG. 4 illustrates a first state of operation of the device of FIG. 1.

The initialisation period 910 comprises the following steps:

Step 911 (Initial filling of radiopharmaceutical to point C): In a first step, the complete tubing is filled with saline, thereby excluding air from the tubing system. For this, valve V1 is switched into a state connecting ports "c" and "b", while valve V2 connects "d" and "e". Pump P2 flushes saline up to point B (cf. FIG. 4). Then the tubing section 4 is inserted into a vial containing saline. Valve V1 is brought into a state connecting ports "a" and "b", while valve V2 still connects "d" and "e". Pump P1 now flushes saline until the tubing is completely filled with saline from point A (cf. FIG. 4) to the destination beyond valve V2, and air is thus completely purged from the system. The tubing section 4 is then inserted into the vial 2 containing the radiopharmaceutical. Valve V1 is brought into a state connecting ports "a" and "b", while valve V2 connects ports "d" and "f". Pump P1 is operated to pump radiopharmaceutical 1 from inlet point A and past point B at valve V1 to some point C in the fill-in section 7. The volume of radiopharmaceutical between points B and C in the fill-in section 7 does not need to be known exactly; it suffices to ensure that the section of tubing from A to B is filled completely with radiopharmaceutical, and that the activity in the volume between B and C is not larger than the desired end activity Ar. The situation at the end of step 911 is illustrated in FIG. 4, where the volume of radiopharmaceutical between points B and C is designated by reference number 21.

Figure 5:
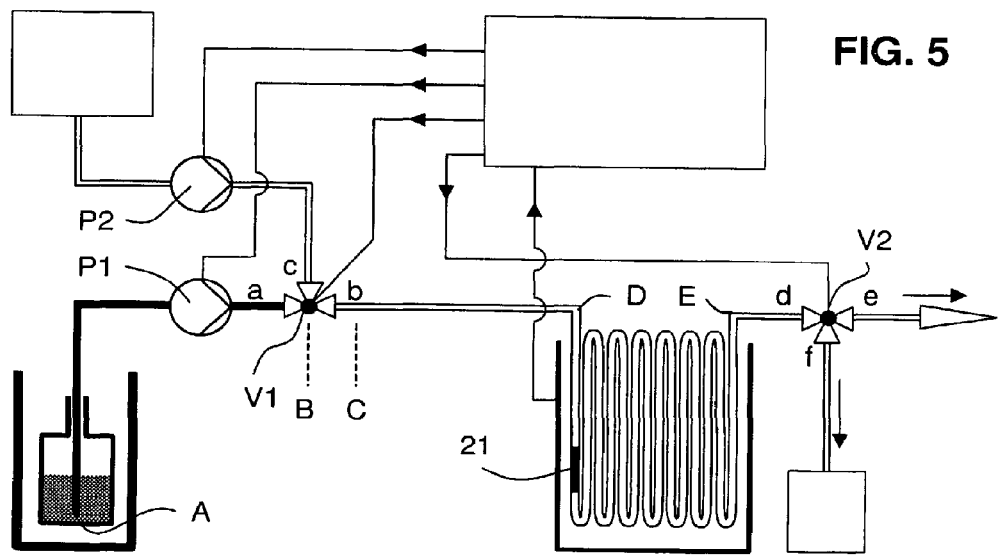
FIG. 5 illustrates a second state of operation of the device of FIG. 1.

Step 912 (Flushing of offset volume to dose calibrator): Valve V1 is now switched to a state in which it connects ports "c" and "b". Pump P2 is operated to pump saline from the saline reservoir 5 towards valve V1. The volume to be pumped is slightly larger than the volume in the fill-in section 7 of the tubing, i.e. slightly larger than the volume between points B and D. This volume need not be known exactly. Thereby, the "offset volume" 21 is moved into the metering section 8. The situation at the end of this step is illustrated in FIG. 5.

Figure 10:
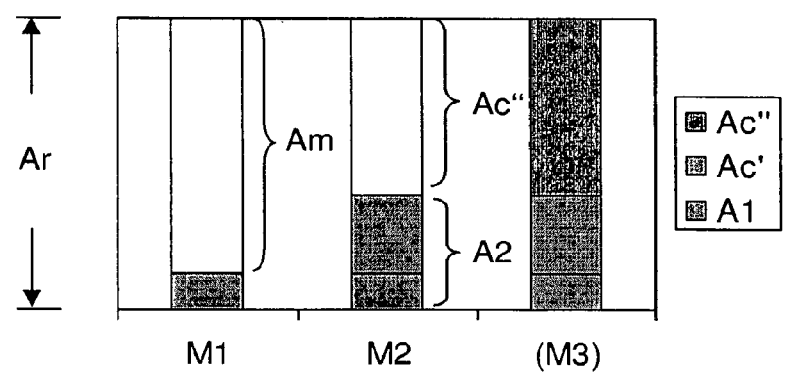
FIG. 10 illustrates the levels of activities measured in various stages of the process of FIG. 9.

Step 913 (Initial determination of activity): The activity of volume 21 in the metering section 8 is measured by the dose calibrator 9 (measurement M1). This activity will be called the "offset activity" A1. The controller 13 now calculates the missing activity Am required to reach a total activity of Ar: Am=Ar−A1. This is illustrated in FIG. 10 in the leftmost column. From this and the estimated concentration of activity in the vial, Cv, the estimated missing volume Va1 still to be delivered is calculated: Va1=Am/Cv. It is important to note that this calculation is still based on the estimate of the concentration of activity in the vial, and the result cannot be expected to be highly accurate. It is further important to note that no knowledge about the offset volume 21 is required in this calculation.

Figure 6:
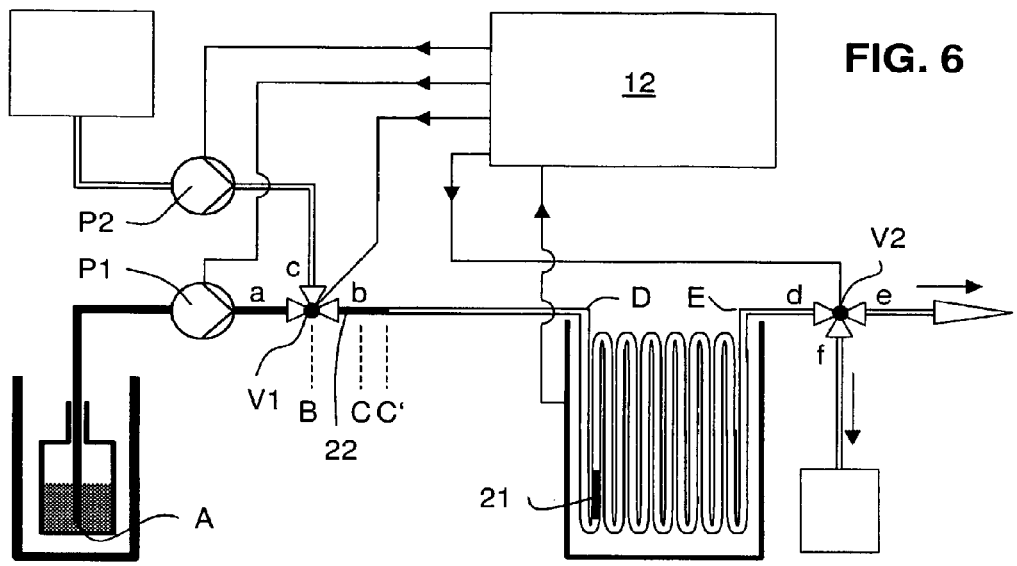
FIG. 6 illustrates a third state of operation of the device of FIG. 1.

This step concludes initialisation 910. In the following calibration phase 920, the following steps are performed:

Step 921 (Filling of radiopharmaceutical to point C'): Valve V1 is switched to a state in which it connects ports "a" and "b". Pump P1 is operated to pump a volume Vc' through valve V1, filling the fill-in section to point C'. This situation is illustrated in FIG. 6, where this volume is designated by reference number 22. Volume Vc' is chosen to be approximately half of the estimated missing volume Va1: Vc'≈Va1/2. It is important to note that volume Vc' is known exactly in system internal units. The exact nature of these units depends on the type of pump used, e.g., the units could be pump revolutions, pump cycles etc. If a volume flow meter is placed in-line with the pump, the units provided by the flow meter can be used as system internal units. Depending on the type of pump and the type of tubing, the resolution of volume in this step can be very small, and even small volumes can be delivered accurately.

Step 922 (Flushing of volume Vc' to dose calibrator): Valve V1 is switched to connect ports "c" and "b". Pump P2 is operated to pump slightly more than the volume between points B and D of saline through valve V1. Thereby, volume 22 (=Vc') of radiopharmaceutical is moved into the metering section 8. The situation at the end of this step is illustrated in FIG. 7.

Step 923 (Calibration of activity): The activity in the metering section 8 is measured by the dose calibrator 9 (measurement M2). This activity level will be called A2. It corresponds to the sum of the offset activity A1 and the activity of the volume Vc', which will be called the "reference activity" Ac'. This is illustrated in the second column of FIG. 10. Now the activity concentration in the vial in system internal units, Cs, is calculated: Cs=Ac'/Vc'=(A2−A1)/Vc'. The system is now calibrated in system internal units.

Step 924 (Determination of volume Vc"): The activity Ac" still required to reach a total activity of Ar is determined: Ac"=Ar−A2. From this, the volume Vc" still to be delivered is calculated in system internal units: Vc"=Ac"/Cs=(Ar−A2)/Cs=(Ar−A2)/(A2−A1)*Vc'.

This completes the calibration phase 920. In the following delivery phase 930, the following steps are performed:

Step 931 (Filling of radiopharmaceutical to point C"): Valve V1 is switched to a state in which it connects ports "a" and "b". Pump P1 is operated to pump the volume Vc" through valve V1, filling the fill-in section to point C". This situation is illustrated in FIG. 8, where this volume is designated by reference number 23.

Step 932 (Flushing of volume Vc" to dose calibrator): Valve V1 is switched to connect ports "c" and "b". Pump P2 is operated to pump slightly more than the volume between points B and D of saline through valve V1. Thereby, volume 23 (=Vc") of radiopharmaceutical is moved into the metering section 8. Optionally, the total activity in the metering section is now measured (optional measurement M3, see right column of FIG. 10). It should correspond exactly to the total desired activity Ar, provided that the volume of the metering section is large enough to hold all three volumes 21, 22 and 23 within this section. The latter condition is can always be fulfilled if the volume of the metering section 8 is at least five times the volume of the fill-in section 7. If a significant discrepancy is detected, the system is stopped.

Step 933 (Delivery to injection needle): Valve V2 is switched to connect ports "d" and "e". Pump P2 is operated to pump at least the volume of the metering section 8, plus the volume of the tubing from the metering section to the injection needle and of the injection needle itself, of saline through valve V1. Thereby, all liquid in the metering section 8 is flushed to the patient, and exactly the required dose of radioactivity is delivered to the patient.

This completes the delivery phase 930. If another injection of the same radiopharmaceutical (to the same or a different patient) is required, operation continues by repeating the calibration and delivery phases 920 and 930. Otherwise, operation stops by a suitable shutdown procedure, which may involve additional cycles of flushing with saline.

When repeating calibration phase 930, no additional initialisation as in phase 910 is necessary, since the metering section 8 has been flushed with saline, and the radiopharmaceutical extends exactly to point B. No activity is present in the metering section 8. Therefore, in the above calculations, A1 can be set to zero in this case, and Am is set to Ar. No further changes are necessary. The three-phase procedure with phases 910, 920 and 930 now simplifies to a two-phase procedure with phases 920 and 930 only.

It will be appreciated that the device of the present invention and the associated method of operation provide a number of inherent safety features. Specifically, there is a high degree of redundancy in the operation of the device, such that even in case of failure of one component, such as a pump or a valve, it is impossible that more than the desired dose will be delivered to the patient. Specifically, by its design the system will only allow the dose present within the metering section 8 to be delivered to the patient. This is because during the actual delivery of the radiopharmaceutical there is no connection between the vial 2 and the fluid delivery line. The discrete nature of the sequential measurements of activity within the metering section 8 is another feature which increases safety: In step 932, the activity in the metering section 8 is actually known beforehand, and measurement M3 just serves to confirm that the right amount of activity is present in the metering section 8. If significant discrepancies are detected between the expected result and the actual measurement, operation will be stopped immediately, and an alarm will be given.

It will also be appreciated that, in normal operation, no radiopharmaceutical will enter the waste reservoir 12. Thus, generation of radioactive waste is minimized.

A device according to the present invention in the embodiment of FIG. 1 has been set up and tested in practice. The device was assembled from standard components available commercially. For the tubing sections 4 and 6, flexible tubing made from silicone with an inner diameter of 1.52 mm was used. The pumps P1 and P2 were peristaltic precision pumps (P1: Ismatec™ ISM 596B, P2: Arcomed™ Volumed™ mVp 5000). The valves V1 and V2 were electrically operated pinch valves available from Bio-Chem Valve Inc. The metering section 8' of tubing had a coil shape with nine windings and a diameter of 3.5 cm, made from fluoroethylene-propylene. A Veenstra VDC 405 dose calibrator was used as activity metering unit/dose calibrator 9. The complete assembly was shielded by a 5 cm lead shield. As a controller 13, a standard personal computer (Compaq Armada E500) equipped with a standard interface card was used. The control algorithm was implemented in LabVIEW™, available from National Instruments™.

This embodiment is especially suitable for the use with radiopharmaceuticals typically used in PET and SPECT applications. The device has been used to deliver radiopharmaceuticals with activity concentrations as high as 1000 MBq/ml to patients, with an absolute precision of as good as 100 microliters and a relative precision of better than 2% of the total activity delivered to the patient.

From the above description, it is clear that numerous variations of the described device and method are possible, and the invention is in no way limited to the above examples.

While the method has been described in a way that the volume of the metering section 8 of tubing is large enough to hold at the same time all volumes of radiopharmaceutical to be injected together, the method can readily be adapted for use with a dose calibrator which measures only one of these volumes at a time. In this case, the activities A1, Ac' and, optionally, Ac" are measured directly and sequentially and need not be calculated. Both variants of the method have in common that the activity of a precisely known volume (in some arbitrary units) is measured, enabling determination of the activity concentration of the radiopharmaceutical.

The method can be extended to take into account the decrease of activity during the dispensing procedure, in a straightforward manner by calculating the decay during the (predetermined) time needed for the dispensing procedure.

The inventive device and method are not only useful for delivering a radiopharmaceutical to a human or animal body, but also in other applications, also of a non-medical nature, in which a precisely known amount of activity is to be delivered to some destination. Accordingly, many variations of the types of tubing, valves, pumps etc. are possible. Specifically, other pump types than peristaltic pumps may be used. In fact, while the use of pumps is preferred, pumps may be omitted if the vial 2, the saline reservoir 5 or both are placed "top-down" in a position higher than valves V1, V2 and the destination 16. Fluid flow is then effected by gravity alone. Instead of pumps, flow meters should then be provided, yielding volume information to the controller 13.

Different types of valves than the above-described two-way pinch valves may be used. Specifically, it may be advantageous to provide, as valve V1, a valve which can be switched to a third state such that liquid can flow between ports "a" and "c". In this way, the sections of tubing between points A and B may be flushed with saline from reservoir 5, without the need of inserting a vial with saline instead of the vial with the radiopharmaceutical during initialisation.

Any suitable activity detector may be used as a dose calibrator 9. Such detectors include standard Geiger-Müller counters, scintillating counters etc., which should be calibrated to yield a sufficiently precise measure of the actual activity in the metering section 8.

Additional safety measures may be taken, such as providing bubble detectors in the fluid delivery path which stop operation immediately if bubbles are detected. Bubble detectors are well known in the art.

LIST OF REFERENCE SIGNS

P1 first pump
P2 second pump
V1 first valve
V2 second valve
a, b, c connections of first valve
d, e, f connection of second valve
A inlet of radiopharmaceutical
B, C, C', C" reference points
D start of metering section
E end of metering section
M1, M2, M3 measurements
A1, A2, Ar, Am, Ac', Ac" activities
1 radiopharmaceutical
2 vial
3 shield
4 tubing
5 saline container
6 tubing
7 tubing
8, 8' metering section
9 dose calibrator
10 tubing
11 injection needle
12 waste
13 controller
21, 22, 23 volumes of radiopharmaceutical
31 sliding element

The invention claimed is:
1. A device for dispensing a radioactive liquid to a destination, the device comprising:
a first valve means;
a fluid delivery path for fluid flow from the first valve means to the destination;
a metering section connected to the fluid delivery path; and
an activity metering unit operable to determine an activity concentration in a radioactive liquid source in system internal units,
wherein the activity metering unit determines a level of radioactivity within the metering section of the fluid delivery path as a radioactive liquid is moved into the metering section,
wherein a volume for a total activity amount is determined based on the activity concentration in the radioactive liquid source in system internal units,
wherein the first valve means is adapted for selectively connecting the radioactive liquid source and a flushing liquid source to the fluid delivery path upstream of the metering section and is adjusted to deliver the total activity amount,
wherein the metering section is capable of holding at least two separate amounts of the radioactive liquid having a total volume containing at least one total activity amount of the radioactive liquid from the radioactive liquid source.

2. The device according to claim 1, wherein the first valve means is adapted for remote operation and the device further comprises a control unit which receives signals from the activity metering unit and controls operation of the first valve means between at least the following states:
a state in which the radioactive liquid source is connected to the fluid delivery path; and
a state in which the flushing liquid source is connected to the fluid delivery path.

3. The device according to claim 1, further comprising:
a second valve means for selectively connecting the fluid delivery path downstream from the metering section to the destination or to a waste reservoir.

4. The device according to claim 1, further comprising:
at least one of a first pump for pumping the radioactive liquid from the radioactive liquid source toward the first valve means and a second pump for pumping the flushing liquid from the flushing liquid source toward the first valve means.

5. The device according to claim 1, wherein the fluid delivery path comprises a fill-in section extending from the first valve means to the metering section, and the metering section is capable of holding a fluid volume which is at least three times the volume of the fill-in section.

6. The device according to claim 1, further comprising an injection needle connected to the fluid delivery path and adapted to inject liquid into a human or animal body.

7. A method of delivering a radioactive liquid to a destination, the method comprising the steps of:
providing a desired level of radioactivity to be delivered to the destination;
determining an activity concentration of a radioactive liquid in a radioactive liquid source in system internal units;
determining a volume for a total activity amount of the radioactive liquid based on the activity concentration of the radioactive liquid in the radioactive liquid source in system internal units;
determining a level of radioactivity within a metering section of a fluid delivery path using an activity metering unit as the radioactive liquid is moved into the metering section, and
adjusting a first valve means connected between at least the radioactive liquid source and a flushing liquid source and a fluid delivery path upstream of the metering section whereby delivery of the total activity amount is made into the metering section, wherein the metering section is capable of holding at least two separate amounts of the radioactive liquid having a total volume containing at least one total activity amount of radioactive liquid from the radioactive liquid source.

8. The method according to claim 7, wherein determining the activity concentration of the radioactive liquid in the radioactive liquid source in system internal units comprises:
transporting a first amount of the radioactive liquid to the metering section of the fluid delivery path;
measuring a reference level of radioactivity of the first amount of the radioactive liquid present in the metering section with the activity metering unit;
from the reference level of radioactivity, calculating a second amount of the radioactive liquid such that the first and second amounts of the radioactive liquid together have a predetermined level of radioactivity;
transporting the second amount of the radioactive liquid to the metering section of the fluid delivery path;
measuring a second level of radioactivity; and
calculating the activity concentration of the radioactive liquid in the radioactive liquid source in system internal units.

9. The method according to claim 8, wherein the first amount of the radioactive liquid is at least 20% of the sum of the first and second amounts of the radioactive liquid.

10. The method according to claim 8, wherein the step of transporting the first amount of the radioactive liquid comprises:
operating the first valve means to connect the radioactive liquid source to the fluid delivery path;
allowing the first amount of the radioactive liquid to flow into the fluid delivery path;
operating the first valve means to connect the flushing liquid source to the fluid delivery path; and
allowing a flushing liquid to flow into the fluid delivery path, whereby the first amount of the radioactive liquid is moved into the metering section of the fluid delivery path.

11. The method according to claim 8, further comprising the step of delivering the first and second amounts of the radioactive liquid to the destination, the step comprising:
operating the first valve means to connect the radioactive liquid source to the fluid delivery path;
allowing the second amount of the radioactive liquid to flow into the fluid delivery path;
operating the first valve means to connect the flushing liquid source to the fluid delivery path; and
allowing a flushing liquid to flow into the fluid delivery path, whereby the first and second amounts of radioactive liquid are moved to the destination.

12. The method according to claim 8, further comprising the steps:
before transporting the first amount of the radioactive liquid to the metering section, transporting an offset amount of the radioactive liquid to the metering section;
measuring an offset level of radioactivity of the offset amount of radioactive liquid present in the metering section with the activity metering unit;
from the offset level of radioactivity and the desired level of radioactivity to be delivered to the destination, calculating the predetermined level of radioactivity; and
delivering the offset amount of radioactive liquid to the destination.

13. The method according to claim 7, wherein the radioactive liquid is a liquid comprising a radiopharmaceutical and wherein the destination is an injection needle for injection of liquid into a human or animal body.

14. A method of delivering a radioactive liquid comprising:
extracting a first amount of a radioactive liquid from a source of radioactive liquid;
measuring a radioactivity level for the first amount of the radioactive liquid;
extracting a second amount of the radioactive liquid from the source of radioactive liquid wherein the second amount is calculated based on the radioactivity level of the first amount to provide a total dose of the radioactive liquid having a predetermined radioactivity level; and
extracting an additional amount of the radioactive liquid from the source of radioactive liquid, wherein the additional amount has a radioactivity level equal to the predetermined radioactivity level.

15. The method of claim 14, wherein the first amount of the radioactive liquid is between 20% and 80% of the sum of the first and second amounts of the radioactive liquid.

16. The method of claim 14, further comprising delivering the first and second amounts of the radioactive liquid after extracting the second amount.

17. The method of claim 14, further comprising:
delivering the additional amount of radioactive liquid having a radioactivity level equal to the predetermined radioactivity level.

18. The method of claim 16, further comprising flushing with a flushing liquid after delivering the radioactive liquid.

19. The method of claim 16, wherein delivering comprises injecting the radioactive liquid into a human or animal.

20. The method of claim 14, further comprising:
transporting the first amount of the radioactive liquid to a metering section where measuring the radioactive level is carried out;
transporting the second amount of the radioactive liquid to the metering section; and
measuring a radioactivity level of the first and second amounts of the radioactive liquid in the metering section.

21. The method of claim 14, further comprising:
measuring a radioactivity level of the additional amount of the radioactive liquid having the radioactivity level equal to the predetermined radioactivity level.

22. The method of claim 14, further comprising:
transporting the additional amount of the radioactive liquid having the radioactivity level equal to the predetermined radioactivity level to a metering section wherein measuring of a radioactivity level of the additional amount of radioactive liquid having the radioactivity level equal to the predetermined radioactivity level is carried out.

23. A method of operation of a device for delivering a radioactive liquid, the method comprising:
extracting a first amount of a radioactive liquid from a source of radioactive liquid;
transporting the first amount of the radioactive liquid to a metering section of a fluid path;
measuring a radioactivity level for the first amount of the radioactive liquid;
extracting a second amount of the radioactive liquid from the source of radioactive liquid wherein the second amount is calculated based on the radioactivity level of the first amount of the radioactive liquid to provide a total dose of radioactive liquid having a predetermined radioactivity level;
transporting the second amount of the radioactive liquid to the metering section;
measuring a radioactivity level for the first amount of the radioactive liquid and second amount of the radioactive liquid;

delivering the first and second amount of the radioactive liquid;

extracting an additional amount of the radioactive liquid from the source of radioactive liquid, wherein the additional amount has a radioactivity level equal to the predetermined radioactivity level;

transporting the additional amount of the radioactive liquid having the radioactivity level equal to the predetermined radioactivity level to the metering section; and delivering the additional amount of the radioactive liquid having the radioactivity level equal to the predetermined radioactivity level.

24. The method of claim 23, further comprising:

flushing the metering section of the fluid path with a flushing liquid after each of the delivering steps.

25. The method of claim 23, wherein each of the delivering steps comprises injecting the radioactive liquid into a human or animal.

26. A method of operation of a device for delivering a radioactive liquid, the method comprising:

extracting a first amount of a radioactive liquid from a source of radioactive liquid;

transporting the first amount of the radioactive liquid to a metering section of a fluid path;

measuring a radioactivity level for the first amount of the radioactive liquid;

extracting a second amount of the radioactive liquid from the source of radioactive liquid wherein the second amount is calculated based on the radioactivity level of the first amount of the radioactive liquid to provide a total dose of radioactive liquid having a predetermined radioactivity level;

transporting the second amount of the radioactive liquid to the metering section;

measuring a radioactivity level for the first amount of the radioactive liquid and second amount of the radioactive liquid;

repeating the steps of extracting a second amount of the radioactive liquid, transporting the second amount of the radioactive liquid, and measuring a radioactivity level until a dose of radioactivity having the predetermined radioactivity level is reached; and delivering the dose.

27. The method of claim 26, wherein delivering the dose comprises injecting the radioactive liquid into a human or animal.

28. The method of claim 26, further comprising flushing the metering section of the fluid path with a flushing liquid after delivering the dose.

29. The method of claim 26, further comprising extracting an additional amount of the radioactive liquid having a radioactivity level equal to the predetermined radioactivity level and delivering the additional amount of radioactive liquid equal to the predetermined radioactivity level.

30. The method of claim 26, further comprising:

measuring the amount of the dose of the radioactive liquid having the radioactivity level equal to the predetermined radioactivity level before delivering the dose.

31. The method of claim 29, further comprising:

flushing the metering section of the fluid path with a flushing liquid after delivering the additional amount of the radioactive liquid having the radioactivity level equal to the predetermined radioactivity level.

32. The method of claim 29, further comprising:

repeating the steps of extracting an additional amount of the radioactive liquid having the radioactivity level equal to the predetermined radioactivity level and delivering the additional amount of the radioactive liquid having the radioactivity level equal to the predetermined radioactivity level.

* * * * *

UNITED STATES PATENT AND TRADEMARK OFFICE
CERTIFICATE OF CORRECTION

| | | |
|---|---|---|
| PATENT NO. | : 8,852,071 B2 | Page 1 of 1 |
| APPLICATION NO. | : 13/965670 | |
| DATED | : October 7, 2014 | |
| INVENTOR(S) | : Buck et al. | |

It is certified that error appears in the above-identified patent and that said Letters Patent is hereby corrected as shown below:

IN THE SPECIFICATION
Column 5, Line 1, delete "sec- and" and insert -- second --, therefor.

IN THE CLAIMS
Column 10, Line 26, Claim 2, delete "the-radioactive" and insert -- the radioactive --, therefor.
Column 14, Line 13, Claim 29, delete "comprising" and insert -- comprising: --, therefor.
Column 14, Line 17, Claim 29, delete "amount of" and insert -- amount of the --, therefor.

Signed and Sealed this
Twenty-second Day of September, 2015

Michelle K. Lee
*Director of the United States Patent and Trademark Office*